US009928585B2

(12) United States Patent
Schirra et al.

(10) Patent No.: US 9,928,585 B2
(45) Date of Patent: Mar. 27, 2018

(54) SPECTRAL IMAGING

(75) Inventors: Carsten Oliver Schirra, St. Louis, MO (US); Gregory Lanza, St. Louis, MO (US); Roland Proksa, Neu Wulmstorf (DE); Ewald Roessl, Ellerau (DE); Axel Thran, Hamburg (DE); Robert Manzke, Sleepy Hollow, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 98 days.

(21) Appl. No.: 13/981,608

(22) PCT Filed: Jan. 12, 2012

(86) PCT No.: PCT/IB2012/050150
§ 371 (c)(1),
(2), (4) Date: Jul. 25, 2013

(87) PCT Pub. No.: WO2012/101537
PCT Pub. Date: Aug. 2, 2012

(65) Prior Publication Data
US 2013/0308847 A1 Nov. 21, 2013

Related U.S. Application Data

(60) Provisional application No. 61/436,711, filed on Jan. 27, 2011.

(51) Int. Cl.
*A61B 6/00* (2006.01)
*G06T 7/00* (2017.01)
*G06T 11/00* (2006.01)

(52) U.S. Cl.
CPC ............ *G06T 7/0012* (2013.01); *A61B 6/481* (2013.01); *A61B 6/482* (2013.01); *G06T 11/005* (2013.01); *G06T 2211/408* (2013.01)

(58) Field of Classification Search
CPC ................ G06T 7/0012; G06T 11/005; G06T 2211/408; A61B 6/481; A61B 6/482
See application file for complete search history.

(56) References Cited

U.S. PATENT DOCUMENTS

| 7,074,183 B2 * | 7/2006 | Castellanos ................... 600/300 |
| 7,713,705 B2 | 5/2010 | Buechler et al. |
| 7,924,968 B2 | 4/2011 | Proksa |
| 7,968,853 B2 | 6/2011 | Altman et al. |
| 8,213,566 B2 | 7/2012 | Roessl et al. |

(Continued)

FOREIGN PATENT DOCUMENTS

| CN | 101785029 | 7/2010 |
| JP | 2004223158 | 8/2004 |
| JP | 2007502676 | 2/2007 |
| JP | 2008161690 | 7/2008 |
| JP | 2009508617 | 3/2009 |

(Continued)

OTHER PUBLICATIONS

Schlomka et al., "Experimental feasibility of multi-energy photon-counting K-edge imaging in pre-clinical computed tomography", Phys. Med. Biol. 53 (2008) 4031-4047.*

(Continued)

*Primary Examiner* — Katrina Fujita

(57) ABSTRACT

A method includes analyzing a spectral projection image of a portion of a subject, generating a value quantifying an amount of a target specific contrast material in a region of interest of the spectral projection image, and generating a signal indicative of a presence of the target in response to the value satisfying a predetermined threshold level.

24 Claims, 3 Drawing Sheets

(56) References Cited

U.S. PATENT DOCUMENTS

| | | | | |
|---|---|---|---|---|
| 2003/0208116 | A1* | 11/2003 | Liang | A61B 5/055 600/407 |
| 2004/0264626 | A1* | 12/2004 | Besson | A61B 6/508 378/4 |
| 2008/0118122 | A1* | 5/2008 | Sirohey | G06T 7/0012 382/128 |
| 2008/0281205 | A1* | 11/2008 | Naghavi et al. | 600/458 |
| 2010/0137711 | A1* | 6/2010 | Hamilton et al. | 600/431 |
| 2010/0185079 | A1* | 7/2010 | Huizenga | A61B 5/055 600/410 |
| 2011/0097273 | A1* | 4/2011 | Proksa | A61B 5/4869 424/9.1 |
| 2011/0123082 | A1* | 5/2011 | Proksa | G06T 11/006 382/131 |

FOREIGN PATENT DOCUMENTS

| | | |
|---|---|---|
| WO | 2008042486 A2 | 4/2008 |
| WO | 2008078231 A1 | 7/2008 |
| WO | 2009049083 | 4/2009 |
| WO | 2010/004460 | 1/2010 |
| WO | 2010007545 | 1/2010 |
| WO | 2010/015953 | 2/2010 |
| WO | 2010046796 | 4/2010 |

OTHER PUBLICATIONS

Hamirani et al., "Atherosclerotic plaque composition among patients with stenotic coronary artery disease on noninvasive CT angiography", Apr. 2010, Coronary Artery Disease 21, 222-227.*

Kolodgie et al., "Localization of Apoptotic Macrophages at the Site of Plaque Rupture in Sudden Coronary Death", American Journal of Pathology, vol. 157, No. 4, Oct. 2000.*

Brendel et al. "Empirical projection-based basis-component decomposition method." Proc. SPIE. vol. 7258. 2009.*

Li et al. "Stress analysis of carotid plaque rupture based on in vivo high resolution MRI." Journal of biomechanics 39.14 (2006): 2611-2622.*

Granton et al. "Implementation of dual- and triple-energy cone-beam micro-CT for postreconstruction material decomposition." Medical physics 35.11 (2008): 5030-5042.*

Cormode, D. P., et al.; Atherosclerotic Plaque Composition: Analysis with Multicolor CT and Targeted Gold Nanoparticles; 2010; Radiology; 256(3)774-782.

Pan, D., et al.; Computed Tomography in Color: NanoK-Enhanced Spectral CT Molecular Imaging; 2010; Chem. Int. Ed. Engl.; 49(50)9635-9639.

Roessl, E., et al.; Preclinical spectral computed tomography of gold nano-particles; Nov. 25, 2010; Nuclear Instruments and Methods in Physics Research; A 648:5259-5264.

Roessl, E., et al.; K-edge imaging in x-ray computed tomography using multi-bin photon counting detectors; 2007; Phys. Med. Biol.; 52:4679-4696.

Hanwen Li, et al., "Contrast agent dose selection based on intravenous pyelography under a dual energy subtraction technique", Journal of Practical Medical techniques, Jun. 2008 vol. 15, No. 18, pp. 2358-2359.

* cited by examiner

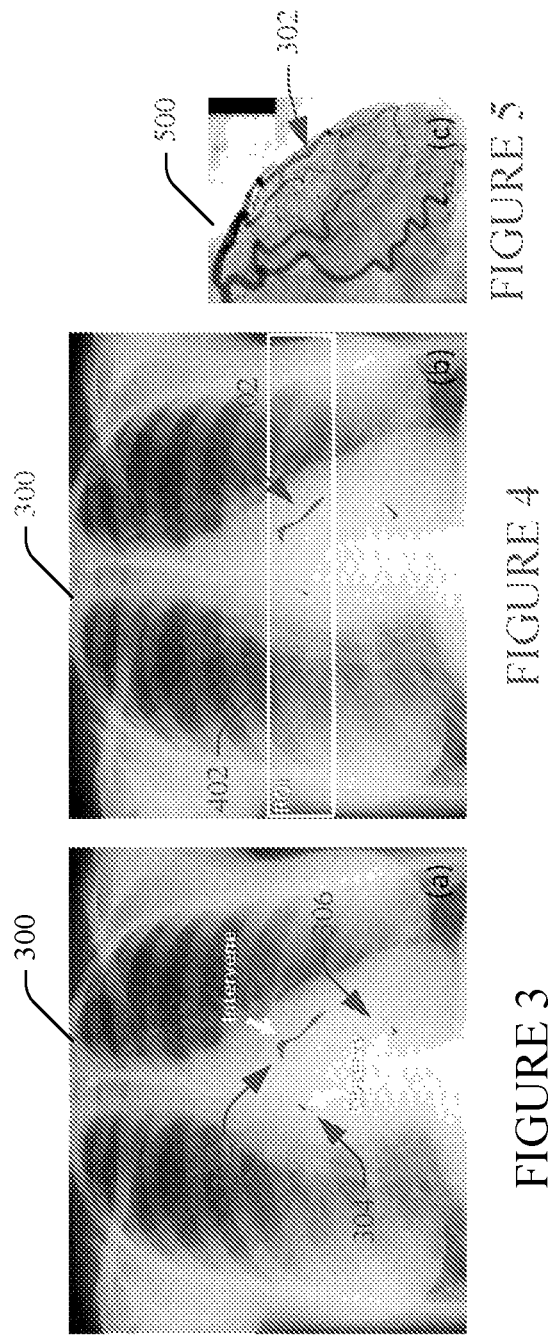

SPECTRAL IMAGING

CROSS REFERENCE TO RELATED APPLICATIONS

This application is a national filing of PCT application Serial No. PCT/IB2012/050150, filed Jan. 12, 2012, published as WO 2012/101537 A1 on Aug. 2, 2012, which claims the benefit of U.S. provisional application Ser. No. 61/436,711 filed Jan. 27, 2011, which is incorporated herein by reference.

FIELD OF THE INVENTION

The following generally relates to spectral imaging and is described with particular application to computed tomography (CT); however, the following is also amenable to other imaging modalities.

BACKGROUND OF THE INVENTION

A person experiencing chest pain has gone to the emergency room (ER). Generally, chest pain may be a symptom of a number of conditions, including cardiac and non-cardiac in origin. Often times, the person has no history of cardiac disease and the origin of the chest pain is unknown. A typical approach to diagnosing the person is to rule out certain causes of chest pain (differential diagnosis) such as myocardial infarction (MI or heart attack), pulmonary embolism, thoracic aortic dissection, etc. A standard procedure of the ER is to test troponin (a protein of muscles) levels of the person, perform an electrocardiogram (ECG) to obtain signals representative of the electrical activity of the heart, and/or admit the person for observation. When the results of such procedures are inconclusive, the person has further undergone invasive coronary angiography, stress testing, surgery, and/or other non-invasive imaging (e.g., a chest x-ray) to facilitate determining the cause of the chest pain.

Computed tomography (CT) is a non-invasive imaging procedure. A conventional CT scanner generally includes an x-ray tube mounted on a rotatable gantry opposite a detector array across an examination region. The rotatable gantry, and hence the x-ray tube, can be rotated, under system control, around the examination region. The rotatable gantry, and hence the x-ray tube, can also be parked or held at a static angular position with respect to the examination region. The x-ray tube is configured to emit radiation that traverses the examination region and is detected by the detector array. The detector array, in response, generates and outputs a signal indicative of the detected radiation. The signal is reconstructed to generate a two dimensional projection image (e.g., a scout/pilot image) or three dimensional volumetric image data, depending on the type of scan performed.

The resulting projection image or volumetric image data includes pixels or voxels that typically are represented in terms of gray scale values corresponding to relative radiodensity. The gray scale values reflect the attenuation characteristics of the scanned subject and/or object, and generally show structure such as anatomical structures within the scanned patient or object. Since the absorption of a photon by a material is dependent on the energy of the photon traversing the material, the detected radiation also includes spectral information, which provides additional information indicative of the elemental or material composition (e.g., atomic number) of the scanned material of the subject and/or object. Unfortunately, conventional CT data does not reflect the spectral characteristics as the signal output by the detector array is proportional to the energy fluence integrated over the energy spectrum.

A spectral CT scanner captures the above-noted spectral characteristics. Generally, a spectral CT scanner may include two or more x-ray tubes configured to emit radiation having different mean spectrums, a single x-ray tube configured to be controllably switch between at least two different emission voltages (e.g., 80 kVp and 140 kVp) during scanning, and/or a single broad spectrum x-ray tube and an energy-resolving detector array with energy-resolving detectors (e.g., with photon counting detectors, at least two sets of photodiodes with different spectral sensitivities, etc.) and discrimination electronics. K-edge spectral imaging leverages the phenomena that high-Z elements tend to attenuate photons to a much higher extent above a particular energy (the K-edge energy of the given element) relative to attenuating photons just below the K-edge energy. The discontinuity in the attenuation behavior can be detected using an energy-resolving detector.

Unfortunately, CT scanners emit ionizing radiation and thus expose the person being scanned to ionizing radiation, which may damage or kill cells and/or increase the risk of cancer. As such CT scans have not become part of the clinical standard for non-invasive differentiation of chest pain. Thus, there is an unresolved need for lowering dose so that CT scanners can become part of the clinical standard for non-invasive differentiation of chest pain and/or other procedures.

SUMMARY OF THE INVENTION

Aspects of the present application address the above-referenced matters and others.

According to one aspect, a method includes analyzing a spectral projection image of a portion of a subject, generating a value quantifying an amount of a target specific contrast material in a region of interest of the spectral projection image, and generating a signal indicative of a presence of the target in response to the value satisfying a predetermined threshold level.

In another aspect, a system includes an analyzer that analyzes a spectral projection image of a portion of a subject and generates a value quantifying an amount of a target specific contrast material in a region of interest of the spectral projection image and a processing component that compares the value with a predetermined threshold level and generates a signal that indicates whether the target specific contrast material is present in the spectral projection image.

In another aspect, a computer readable instructions encoded on computer readable medium, which, when executed by a processor of a computing system causes the processor to: generate a value quantifying an amount of a target specific contrast material in a region of interest of a spectral projection image of a portion of a subject, generate a signal indicative of a presence of the target in response to the value satisfying a predetermined threshold level, generate a recommendation that recommends a course of action for the subject based on at least one of the spectral projection image, the value or the signal, and display at least one of spectral projection image, the threshold, the value or the signal.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 3 illustrates an example K-edge image for identifying a presence of a target.

FIG. 4 illustrates an example K-edge image for planning an imaging procedure.

FIG. 5 illustrates an example volume image generated based on a scan planned via a K-edge image.

DETAILED DESCRIPTION OF EMBODIMENTS

The following provides a non-limiting decision support framework that generates information that facilitates diagnosis of certain symptoms of and subsequent action for a patient. In one non-limiting instance, the framework processes a spectral-CT x-ray projection image (e.g., a spectral scout or pilot image) of the patient. Generally, the spectral-CT x-ray projection image may be similar to a conventional x-ray projection but with the addition of spectral information and can be obtained from a contrast-enhanced spectral-CT scan of the patient using one or more target-specific contrast agents. The framework then identifies one or more "hot spots" of the one or more administered target-specific contrast agents in the spectral-CT x-ray projection image. For a chest pain patient, the above may include performing a contrast-enhanced spectral-CT scan of the patient using a ruptured plaque targeted contrast agent, and processing the resulting spectral-CT x-ray projection image (and/or quantitative information obtained there from), which indicates whether any of the plaque has ruptured, for the differential diagnosis of the chest pain and, optionally, subsequent treatment planning. As described herein, using such a spectral-CT x-ray projection image along with the certain workflow may reduce patient radiation exposure or dose relative to a configuration in which the spectral-CT x-ray projection image and/or the certain workflow are not employed.

Figure 1:
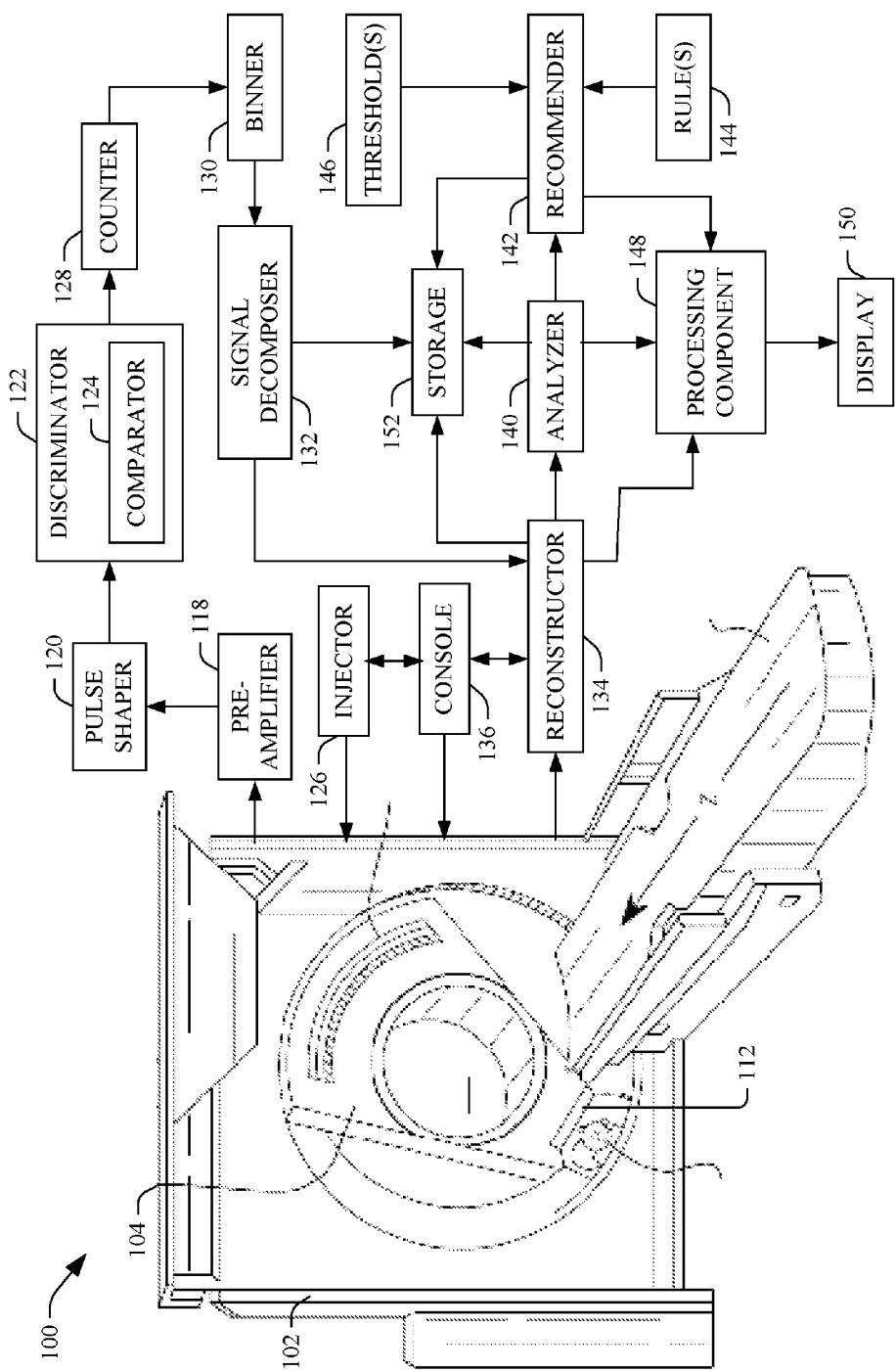
FIG. 1 schematically illustrates an example imaging system in connection with various components for processing the output of the system.

FIG. 1 illustrates an example imaging system 100 such as a computed tomography (CT) system. The imaging system 100 includes a generally stationary gantry 102 and a rotating gantry 104, which is rotatably supported by the stationary gantry 102. The rotating gantry 104 rotates around an examination region 106 about a longitudinal or z-axis. A subject support 108 such as a couch supports a human or animal patient or an object in the examination region 106. The subject support 108 is movable in coordination with scanning so as to guide the subject or object with respect to the examination region 106 for performing a two dimensional projection (e.g., scout/pilot, etc.) or volume (e.g., helical/spiral, axial, etc.) scan of the subject or object.

A radiation source 110, such as an x-ray tube, is supported by the rotating gantry 104 and emits poly-energetic/chromatic radiation. A collimator 112 collimates the radiation beam to produce a generally cone, fan, wedge, cone or otherwise shaped radiation beam that traverses the examination region 106 and the portion of the subject or object disposed therein. For projection scans, the rotating gantry 104 and hence the radiation source 110 may be held at a static angular location with respect to the examination region 106. In another instance, the rotating gantry 104 rotates and a projection image is created from data acquired at a same or similar angular location. For volume scans, the rotating gantry 104 and hence the radiation source 110 rotates around the examination region 106 while the radiation source 110 emits radiation.

A radiation sensitive detector array 116 detects photons that traverse the examination region 106. The illustrated radiation sensitive detector array 116 is an energy-resolving detector such as a direct conversion detector (e.g., Si, Ge, GaAs, CdTe, CdZnTe, etc.) or a scintillator-based multi-spectral detector (e.g., a double decker detector) that includes at least two scintillators having different x-ray energy sensitivities and at least two corresponding photo-sensors having corresponding optical sensitivities. A non-limiting example of a double decker detector is described in patent application Ser. No. 11/912,673, filed Oct. 26, 2007, and entitled "Double Decker Detector for Spectral CT," the entirety of which is incorporated herein by reference. The radiation sensitive detector array 116 generates an electrical signal, such as an electrical current or voltage signal, for a detected photon. The radiation sensitive detector array 116 may include one or more rows of detector elements along the z-axis direction.

A pre-amplifier 118 amplifies the electrical signal output by the detector 116. A pulse shaper 120 processes the amplified electrical signal and generates a pulse such as voltage or other pulse indicative of the energy of the detected photon. Energy discriminator 122 energy discriminates the pulse. In the illustrated example, the energy discriminator 122 includes a comparator 124, including one or more sub-comparators, which compares the amplitude of the pulse with two or more different energy thresholds, which correspond to different energies of interest. The comparator 124 produces an output signal indicative of the energy of the photon based on the comparison.

A counter 128 increments a count value for each threshold based on the output of the energy discriminator 122. For instance, when the output of the comparator 124 for a particular threshold indicates that the amplitude of the pulse exceeds the corresponding threshold, the count value for that threshold is incremented. Energy binner 130 energy bins the signals and, hence, the photons into two or more energy bins based on the counts. Each energy bin encompasses an energy range or window. For example, a bin may be defined for the energy range between two thresholds, where a photon resulting in a count for the lower threshold but not for higher threshold would be assigned to that bin.

A signal decomposer 132 decomposes the energy-resolved signals into various energy dependent components. For example, in one instance a detected energy-resolved signal is decomposed into a Compton component, a photo-electric component, and one or more K-edge components representative of one or more K-edge materials, for example, in a contrast material. With embodiments in which the contrast material includes a K-edge material, the K-edge component generally reflects the contrast material, whereas the Compton and photo-electric components are used to reflect the anatomical structure. It is to be appreciated that a maximum likelihood and/or other decomposition technique may be used. An example decomposition approach is described in application serial number PCT/IB2007/055105, filed on Dec. 14, 2007, which claims the benefit of provisional application serial number EP 06126653.2, filed on Dec. 20, 2006, both of which are incorporated in their entirety herein by reference.

A reconstructor 134 selectively reconstructs the detected signals. In one instance, this includes reconstructing the Compton, photo-electric, and/or K-edge components, individually or in combination, for scout/pilot and/or volume scans. With embodiments in which the contrast agent includes a K-edge material, the K-edge component can be reconstructed to generate contrast material image showing the amount of contrast material in connection with the tissue of interest. Where the image is a scout/pilot image, the K-edge image can be used to plan a subsequent pilot/scout and/or volume scan of the patient, for example, based on one or more regions of interest of the image in which contrast material is present. One or more anatomical structural images may also be reconstructed based on one or more of the decomposed components. Furthermore, a contrast material image and a structural image may be superimposed and/or otherwise combined into a single image.

A general purpose computer serves as an operator console 136. The console 136 includes a human readable output device such as a monitor or display and an input device such as a keyboard and mouse. Software resident on the console 136 allows the operator to interact with the scanner 100 via a graphical user interface (GUI) or otherwise. This interaction may include selecting a type of scan such as a scout/pilot or a volume scan, selecting an imaging protocol to employ such as a spectral protocol like a K-edge imaging or other spectral protocol, initiating scanning, etc.

An injector 126 is configured to inject a contrast material(s), for example, for a contrast enhanced imaging procedure. For cardiac applications, a suitable contrast agent includes a ruptured plaque targeted contrast agent. Other cardiac and/or non-cardiac contrast agents are also contemplated herein. The illustrated injector 126 is controlled by the console 136, which may trigger or invoke in the injector 126 to administer the contrast material in coordination with invoking scanning such that peak contrast uptake and enhancement by tissue of interest is scanned during a single respiratory cycle. A contrast agent can additionally or alternatively be manually administered by a clinician or the like. Where the contrast agent is manually administered, the injector 126 can be omitted.

With further respect to the contrast agent, generally, a suitable contrast material may include one or more k-edge components. For example, the contrast material may include a contrast agent with target (e.g., tissue) specific nano-particles, which have an affinity to the particular target, with a suitable K-edge material to be imaged by the imaging system 100. Such nano-particles can be based on elements such as bismuth, gold, gadolinium, and/or other elements with K-edge values within the diagnostic x-ray energy bandwidth (e.g., 20-140 keV). An example application of spectral CT using a suitable contrast material is discussed in "Computed Tomography in Color: NanoK-Enhanced Spectral CT Molecular Imaging," Pan, et al., 2010 Angew. Chem. Int. Ed. 49, 9635-9639.

An analyzer 140 analyzes the reconstructed data from the reconstructor 134. Such data may include, for a scout/pilot and/or a volume scan, the decomposed K-edge component, Compton component and photo-electric component, the K-edge component, Compton component, photo-electric component and/or combination image(s). In one instance, the analyzer 140 quantifies (e.g., generates a numerical value for) the amount of contrast material in connection with the tissue of interest based on the K-edge image and generates a signal indicative of the quantified amount. The quantified amount may include a global value representing all of the tissue of interest and/or one or local values representing predetermined sub-portions of the tissue of interest. Generating such information based on scout/pilot data may reduce patient dose and scan time relative to a configuration in which such information is generated based on volume scan data.

A recommender 142 generates a signal indicative of a recommendation based on the quantified amount (e.g., global and/or local) of contrast material. In the illustrated embodiment, the recommender 142 generates the recommendation based on one or more rules 144 and one or more threshold values 146. By way of example, a rule may indicate that if the amount or level of contrast agent is greater than a threshold value, then the recommender 142 will generate a signal indicating that the patient should receive immediate or near term attention, and that if the amount or level of contrast agent is less than the threshold value, then the recommender 142 will generate a signal indicating that the patient does not require immediate or near term attention.

Other rules may be based on a location within a patient, a size of the area including an amount that exceeds the threshold, patient information (e.g., age, health state, medical history, etc.), clinician preferences, facility preferences, clinical guidelines, national standards, etc. Optionally, additional or supplemental information may be included with a recommendation. For example, where the quantified level exceeds the threshold but the rules indicate that the attention is not required due to the size of the area, the additional or supplemental information may indicate that the size of the area is too small for intervention. A suitable recommendation may also be no recommendation or absence of a recommendation. In this case, the signal may not even be generated. In some embodiments, the recommender 142 is omitted.

A processing component 148 processes at least one or more of the reconstructed data, the quantified level of contrast material, and the recommendation. Such processing may include combining such data for display via a display 150. The display 150 can be part of various systems and/or devices such as a decision support system, an imaging scanner, a smartphone, a PACS, etc. Known and/or other image processing tools (e.g., zoom, pan, segment, etc.) can also be presented via the display and used to manipulate images and/or invoke other functionality. In one instance, the data is concurrently displayed such that the display 150 visually displays one or more structural images, one or more contrast images, the quantified level (e.g., numerically and/or through color coding, highlighting, etc.), and the recommendation. Such data can be individually displayed or one or more of such information can be combined and displayed, and/or displayed differently depending on the location of the display 150, the user, etc.

For example, FIG. 3 (described in greater detail below) shows an example display 150 of spectral scout/pilot images visually showing several areas of probable plaque along with indicia recommending intervention ("Intervene") and observation ("Observe") along with arrows pointing to the corresponding plaque. In, FIG. 4 (described in greater detail below), the display 150 shows the spectral scout/pilot images visually showing the several areas of probable plaque along with a recommended region of interest (ROI) for subsequently scanning the plaque recommended for intervention ("Intervene"). Other information can also be presented such as recommended scan protocols, user selectable menu entries allowing the user to select a recommended scan protocol to load to a scanner to scan the patient, information regarding to accept and/or reject recommendations, and/or other information.

In general, the output of the processing component 148 can used employed in various situations, including, but not limited to, emergency room decision support, differential diagnosis, interventions, interventional radiology or x-ray, multimodality suites, etc. By way of example, where the contrast agent includes a ruptured plaque targeted contrast agent, the CT data may indicate whether any of the plaque has ruptured, and this information can be used in the differential diagnosis of chest pain and subsequent treatment planning and/or imaging.

For example, where the CT data shows that ruptured plaque exists or likely exists, this data can be used to identify a subsequent medical and/or imaging procedure and schedule the identified medical and/or imaging procedure, automatically, semi-automatically with user interaction, and/or manually by a user. In one instance, this includes the processing component 148 interacting with various medical facility information systems such a radiology, laboratory, admitting, surgery, hospital, etc.

Recommendations and/or responses thereto can be stored in a database, analyzed, and/or otherwise utilized. An example of such analysis includes evaluating the recommendation and data in view of historical data, rules, etc. to facilitate determining whether the recommendation includes a false positive.

The processing component 148 may optionally be configured to send a notification (e.g., a page, a telephone call, a text message, an email, an instant message, etc.) to another device (e.g., a pager, a cell or smart phone, a desktop or portable computer, etc.). The notification may, for example, include the recommendation and/or at least a sub-set of the other information. Where the recommendation indicates that the patient may require immediate attention, the processing component 148 may send an alarm notification to the patient's physician, the attending physician, a radiologist, a surgeon, a nursing central monitoring station, security, and/or other predetermined personnel.

Where the recommendation indicates that the patient may require attention, but not immediate, the processing component 148 may send a warning notification. The difference between immediate attention, a warning, and general information by indicated through indicia such as a priority value, a color, audio, and/or other readily recognizable visual and/or audible information. The recipient may respond, through an electronics device, acknowledging receipt and/or indicating an action to be perform by them and/or other personnel. In one instance, the response may be through a smartphone application.

Storage 152 can be used to store one or more of the decomposed data, the reconstructed data, the reconstructed decomposed data, the quantified information, the recommendation, the combined data, and/or other information. The storage 152 is shown as a single component; however, it is to be understood that the storage 152 may include a plurality of storage units, including storage local to the system 100, storage external from the system 100, and/or storage distributed amongst different location, local and/or remote. It is to be understood that the storage 152 is physical memory and not a transitory signal.

Variations are contemplated.

In the illustrated embodiment, the system 100 includes the single radiation source 110. In another embodiment, the system 100 includes two or more radiation sources 110, arranged at different angular locations with respect to each other in the x/y plane, where at least two of the radiation sources 110 emit radiation with different energy spectra. At least two of the two or more radiation sources 110 can be concurrently or individually employed during a same scan and are configured to emit similar or different mean emission spectrums.

Additionally or alternatively, the radiation source 110 is configured to switch between two or more emission voltages, for example, between at least two different emission voltages in a range from 10 kVp to 160 kVp. A source controller or the like can switch the radiation source voltage from scan to scan, between integration periods of a scan, within an integration period, and/or otherwise. As a result, radiation beams having different mean emission energy spectra can be generated and used to scan an object or subject.

In the illustrated embodiment, the system 100 includes the scintillator/photosensor based detector array 116. In another embodiment, the detector array 116 includes photon counting detectors. In this instance, an example of a suitable decomposition algorithm is described in "K-edge imaging in x-ray computed tomography using multi-bin photon counting detectors," E. Roessl and R. Proksa, 2007 Phys. Med. Biol. 52 4679-4696.

An example use-case scenario is now discussed. It is to be understood that this use-case is presented for explanatory purposes and is not limiting.

It is to be appreciated that the ordering of the below acts is for explanatory purposes and not limiting. As such, other orderings are also contemplated herein. In addition, one or more of the acts may be omitted and/or one or more other acts may be included.

At 202, a target specific contrast material is administered to the patient. In this example, the target specific contrast material targets ruptured plaque.

At 204, the administered target specific contrast material is given time to target ruptured plaque. A suitable amount of time can be predetermined based on historical, empirical and/or other data.

At 206, a spectral scout/pilot scan protocol is identified for scanning the patient. This act may include identifying at least a begin scan location of the patient. This can be determined via moving the subject support 108 to a location in the examination region 106 such that the region of interest of the patient will be scanned.

At 208, the patient is scanned using the selected spectral scout/pilot scan protocol.

At 210, the acquired data is decomposed. In this example, this is achieved via the signal decomposer 132, as described herein, to obtain at least a K-edge (or contrast material) component, which includes information indicative of the contrast in the scanned region. The signal decomposer 132 can also be used to generate Compton and/or photo-electric components.

At 212, at least the K-edge component is reconstructed, producing a K-edge projection image. Where an anatomical component has been generated, an anatomical projection image can also be generated. In addition, a combination projection image can be generated by reconstructing the combination of the components and/or combining the contrast material projection image and the anatomical projection image.

At 214, the amount (global and/or local) of contrast material in the tissue of interest is determined based on the projection image. The amount can be based on voxel intensity and/or otherwise.

At 216, the target (ruptured plaque in this example), if any, is identified based on the projection image. For example, in this example, ruptured plaque is identified as voxels having amounts of contrast material that satisfy a predetermined threshold level. This can be determined through observation by a clinician and/or a computer executing suitable computer software.

At 218, if the target (again, ruptured plaque in this example) is identified, then appropriate course of action is determined. For example, if ruptured plaque is identified, the patient may be referred for coronary catheterization, surgery, observation, and/or other procedure. If ruptured plaque is absent, the patient may be discharged, observed, etc. rather than under a procedure such as catheterization, surgery, etc.

The determination of whether and/or which procedure should be performed is determined by a clinician, who may base the decision at least in part on a recommendation from the recommender 142, or automatically, for example, in connection with a decision support systems.

Turning briefly to FIG. 3, an example spectral scout/pilot projection image 300 is shown. In this example, the projection image 300 includes contrast information 302, 304 and 306 that indicates ruptured plaque is present. In this example, the region 302 has been identified for intervention, and the regions 304 and 306 have been identified for observation.

Figure 2:
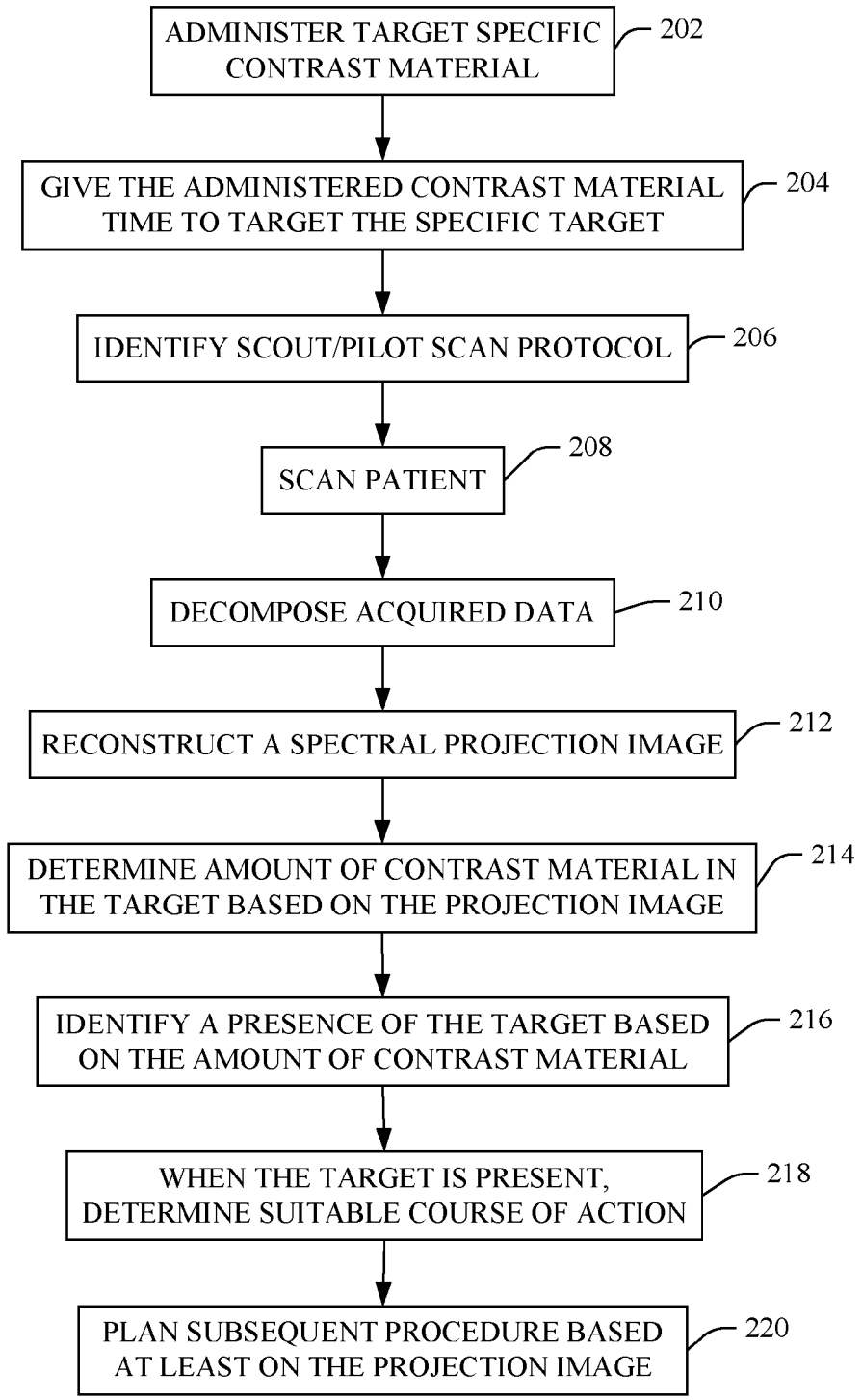
FIG. 2 illustrates an example method.

Returning to FIG. 2, at 220, one or more of the component projection images can be used to plan a subsequent procedure. For example, the one or more projection images can be used to plan a catheterization, a surgery, a subsequent imaging procedure, etc.

Turning briefly to FIG. 4, the spectral scout/pilot projection image 300 has been used to plan a scan around the region 302, as shown by a region of interest (ROI) window 402. FIG. 5 shows reconstructed volumetric three dimensional image data 500 from a volume scan planned based on the ROI 402 in FIG. 4. The region 302 can be seen in the reconstructed volumetric three dimensional image data 500.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

It is to be appreciated that one or more of the components discussed herein (e.g., the signal decomposer 132, the console 136, the reconstructor 134, the analyzer 140, the recommender 142, the processing component 148, etc.) can be implemented via one or more processors executing one or more computer readable instructions encoded or embodied on computer readable storage medium such as physical memory which causes the one or more processors to carry out the various functions described herein and/or other functions. Additionally or alternatively, the one or more processors can execute instructions carried by transitory medium such as a signal or carrier wave.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
analyzing a spectral computed tomography (CT) projection image of a portion of a human subject generated by a spectral CT imaging scan of the human subject with a target specific contrast material that targets ruptured plaque in the cardiovascular system of the human subject;
generating a value quantifying a concentration of the target specific contrast material in a region of interest of the spectral projection image; and
generating a signal indicative of a presence of the targeted ruptured plaque greater than a predetermined threshold level in response to the generated value satisfying the predetermined threshold level.

2. The method of claim 1, wherein the target specific contrast material includes a K-edge material and the signal indicates a presence of the K-edge material when the value satisfies the predetermined threshold level.

3. The method of claim 2, wherein the signal indicates an absence of the K-edge material when the value does not satisfy the predetermined threshold level.

4. The method of claim 1, further including:
scanning the chest portion of the human subject with at least one of a pilot spectral CT scan or a scout spectral CT scan which generates the spectral computed tomography (CT) projection image with the target specific contrast material that targets ruptured plaque in the cardiovascular system of the human subject.

5. The method of claim 1, wherein the value represents pixel intensity.

6. The method of claim 1, further comprising:
generating a recommendation that recommends a course of action for the subject based on the presence of the targeted ruptured plaque at least one of the spectral CT projection image or the signal.

7. The method of claim 6, wherein the recommendation invokes automatic scheduling a subsequent medical or imaging examination for the human subject.

8. The method of claim 6, further comprising:
displaying, concurrently, the spectral CT projection image and at least one of the value, the threshold, the signal or the recommendation.

9. The method of claim 1, further comprising:
planning a subsequent projection scan of locations of the targeted ruptured plaque based on at least one of the spectral CT projection image or the signal.

10. The method of claim 1, further comprising:
planning a subsequent volume scan of locations of the targeted ruptured plaque based on at least one of the spectral CT projection image or the signal.

11. The method of claim 1, further comprising:
planning a medical procedure for the human subject based on the presence of the targeted ruptured plaque indicated in at least one of the spectral CT projection image or the signal.

12. The method of claim 1, further comprising:
performing a differential diagnosis of chest pain of the subject based on the presence of the targeted ruptured plaque indicated in at least one of the spectral CT projection image or the signal.

13. The method of claim 12, further comprising:
decomposing projection data, which is acquired during a contrast enhanced projection scan of the subject, into at least a K-edge component; and
reconstructing the K-edge component to generate the spectral projection image.

14. The method of claim 13, further comprising:
decomposing the projection data into a Compton component and a photo-electric component; and reconstructing the Compton component and the photo-electric component to generate a Compton component projection image and a photo-electric component projection image.

15. A system, comprising:
a radiation sensitive detector array configured to detect photons traversing the examination region of a human subject with a target specific contrast material that targets ruptured plaque and includes at least one of a direct conversion detector or a scintillator-based multi-spectral detector of at least two scintillators having different x-ray energy sensitivities and at least two corresponding photosensors having corresponding optical sensitivities;
a reconstructor including one or more processors configured to selectively reconstruct the detected photons into a spectral projection image;
an analyzer including the one or more processor configured to analyze a spectral projection image of a portion of the human subject and generate a value quantifying a concentration of the target specific contrast material targeting ruptured plaque in a region of interest of the spectral projection image; and
a processing component including the one or more processors configured to process the value with a predetermined threshold level and generate a signal that indicates whether the generated value of the target specific contrast material present in the spectral projection image is greater than the predetermined threshold level.

16. The system of claim 15, wherein the value represents a level of contrast in one of a plurality of regions of interests for a same tissue of interest.

17. The system of claim 15, wherein the value represents a summation of respective levels of contrast in a plurality of regions of interests for a same tissue of interest.

18. The system of claim 15, further comprising:
a recommender including one or more processors configured to generate a recommendation indicative of a course of action for the human subject based on the target specific contrast material targeting ruptured plaque in at least one of the spectral projection image or the value.

19. The system of claim 18, wherein the recommendation indicates the human subject should receive immediate or near term attention, in response to the value satisfying the threshold, and the recommendation indicates the subject does not need immediate or near term attention, in response to the value not satisfying the threshold.

20. The system of claim 19, wherein the recommendation is also based on at least one of a location or a size of the targeting ruptured plaque, patient information, a clinician preference, a facility preference, a clinical guideline, or a national standard.

21. The system of claim 18, wherein the processing component sends an electronic notification which is received by an electronic device of a recipient, wherein the electronic notification includes at least a signal indicative of the recommendation.

22. The system of claim 21, wherein the notification includes information indicative of a priority of the recommendation.

23. The system of claim 15, wherein the processing component displays at least one of the spectral projection image, the value, the threshold, or the signal.

24. Computer readable instructions encoded on a non-transitory computer readable storage medium, which, when executed by a processor of a computing system causes the processor to:
generate a value quantifying a concentration of a target specific contrast material targeting ruptured plaque in a region of interest of a spectral projection image of a portion of a human subject;
generate a signal indicative of a presence of the targeted ruptured plaque in response to the value greater than a predetermined threshold level;
generate a recommendation that recommends a course of action for the human subject based on the presence of the targeted ruptured plaque in at least one of the spectral projection image, the value or the signal; and
display at least one of spectral projection image, the threshold, the value or the signal.

* * * * *